US00PP11576P

United States Patent [19]

Werner et al.

[11] Patent Number: Plant 11,576

[45] Date of Patent: Oct. 17, 2000

[54] PEACH TREE NAMED 'CORINTHIAN MAUVE'

[76] Inventors: Dennis James Werner, 268 Kilgore Hall, Horticultural Science Department, North Carolina State University; Steve Martin Worthington; Layne Karlton Snelling, both of 59 Kilgore Hall, Horticultural Science Department, North Carolina State University, all of Raleigh, N.C. 27695-7609

[21] Appl. No.: 09/146,220

[22] Filed: Sep. 2, 1998

[51] Int. Cl.[7] ..... A01H 5/00

[52] U.S. Cl. ..... Plt./196

[58] Field of Search ..... Plt./194, 187, 199, Plt./191, 180, 196

*Primary Examiner*—Howard J. Locker
*Assistant Examiner*—Wendy A Baker

[57] ABSTRACT

A new and distinct cultivar of peach tree called 'Corinthian Mauve' is provided that demonstrates narrowly columnar growth habit, a vigorous growth rate, green foliage, and an abundance of mauve-colored, double flowers. The new cultivar produces very few fruit, and is intended for use as a Spring flowering ornamental plant in the home landscape.

2 Drawing Sheets

SUMMARY OF THE INVENTION

The new and distinct variety of peach (*Prunus persica* (L.) Batsch) originated as a second generation descendant from a hand pollinated cross of Norht Carolina selection. 'NC174RL' nectarine (non-patented) × a selection of Japanese 'Pillar ' peach made in 1983 at the Sandhills Research Station at Jackson Springs, N.C. The parent plants used in this hybridization have not been named and released and are unavailable in commerce.

The seeds resulting from this controlled hybridization were germinated in a greenhouse at North Carolina State University, Raleigh, N.C. in the Fall of 1983 and planted in the field in Spring of 1984. These trees were grown to maturity; trees were self pollinated in Spring of 1988, and the resultant seed was harvested in August 1988. This seed was sown directly in the field in November 1988, and seedlings flowered in 1991. One seedling, designated NC174RLxPil-271, was selected for its green foliage color, narrowly columnar growth habit, and heavy production of mauve-colored double flowers.

During 1993 and 1996, the original plant selection was propagated asexually by grafting of vegetative buds onto a peach seedling rootstock, cultivar 'Lovell', at the Sandhills Research Station. A grafted tree of the variety was established at the North Carolina State University Lake Wheeler Field Laboratory Research Station in Rale N.C.. Subsequently, a larger test planting has been established with asexually multiplied plants at the Sandhills Research Station, at the above noted location.

The new variety has routinely been asexually multiplied by grafting, specifically 'T' and chip budding. It readily forms a graft union with 'Lovell' peach rootstock and resumes normal growth. During all asexual propagation, the characteristics of the original plant have been maintained and no aberrant phenotypes have appeared.

Test plantings at the two research station locations noted above, which vary considerably in soil and climatic conditions, demonstrate this variety to be widely adapted to differing soil and climatic conditions.

Plants and fruit of this new variety differ phenotypically from its antecedents. The new variety produces mauve-colored double flowers, differing from the single pink flowers of 'NC174RL' and the double pink and white variegated flowers of the Japanese 'Pillar' Peach antecedent. Leaf color is green, growth habit is narrowly columnar, and fruit are pubescent (peach), distinguishing it from the 'NC174RL' nectarine antecedent. Fruit of this new variety are small and of poor quality, and are of no commercial importance.

Plants of the new variety are very vigorous and grow rapidly after establishment of trees in the field. Young trees have averaged 3–4 feet of growth per year. A four-year-old tree measured in Raleigh, N.C. was 14 feet in height and 4.2 feet in spread, with spread measured 6 feet above ground level. Trunk diameter (girth) on the same tree was 3.9 inches one foot above ground level. Plants are narrowly columnar in growth habit. The angle between the trunk and lateral branches of 'Corinthian Mauve' measure between 5 to 20 degrees, in comparison to non-columnar peach varieties such as 'Contender', which typically measure between 35 to 50 degrees.

Flowering sometimes occurs in the second year of growth, but more commonly trees begin flowering in the third year after establishment. Flowers are fully double, mauve-colored, and very attractive. Newly emerged flowers are medium pink/mauve in color (R.H.S. 55D). Individual flowers darken as they age, such that mature 7 to 10day-old flowers are deep pink/mauve (R.H.S. 68A). A range of color shades between these two extremes will occur on different flowers on the plant based on individual age differences in the flowers. Flowering usually begins in mid-March in Raleigh, N.C.; the date of first bloom ranges from March 15 to March 30. Full bloom typically occurs between March 25 to April 10, depending on weather conditions. Bloom duration is typically 10–14 days, and individual flowers last about 7–10 days, depending on temperature during bloom. The chilling requirement is estimated to be 950 hours below 4 C., based on comparison of flowering time to peach cultivars 'Contender' (unpatented), 'Winblo' (unpatented), and 'Clayton' (unpatented) at the Raleigh, N.C. test location.

While 'Corinthian Mauve' is a self-fruitful peach variety, fertility of flowers is poor, and fruit set is generally low in most years, for unknown reasons, unrelated to the pollination requirements of the tree. It is estimated that less than 1% of flowers produced set fruit. Fruit are very small, bitter tasting, and of no horticultural importance in this variety. Fruit ripen in mid to late August in Raleigh, N.C.

'Corinthian Mauve' possesses double, mauve colored flowers, distinguishing it from 'Corinthian White' (co-pending U.S. Plant Pat. application Ser. No. 09/146,219), which possesses double, white colored flowers showing no pigment. 'Corinthian Mauve' differs from 'Corinthian Rose' (co-pending U.S. Plant Pat. application Ser. No. 09/143,338) in having leaves and mauve-colored flowers in contrast to the dark purple leaves and dark pink flowers of 'Corinthian Rose'. 'Corinthian Mauve' differs from 'Corinthian Pink' (co-pending U.S. Plant Pat. application Ser. No. 09/143,339) in having green leaves and mauve colored flowers in contrast to the light purple leaves and light pink flowers of 'Corinthian Pink'.

The new variety has been named the Corinthian Mauve cultivar.

BRIEF DESCRIPTION OF THE DRAWINGS

The accompanying photographs show typical specimens of the entire tree during and after flowering, and close-up pictures of the flowers in color as nearly true as it is reasonably possible to make in a color illustration of this character.

DETAILED DESCRIPTION OF THE NEW VARIETY

Figure 1:
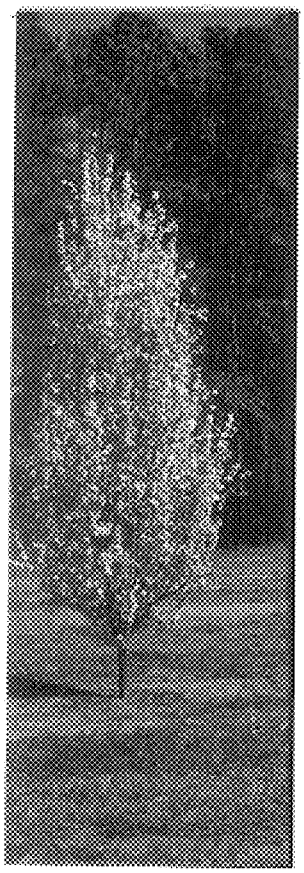
FIG. 1 shows a four year old tree of 'Corinthian Mauve' in full bloom at Raleigh, N.C., showing the narrowly columnar tree architecture, flower color, and heavy flowering characteristics.
Figure 2:
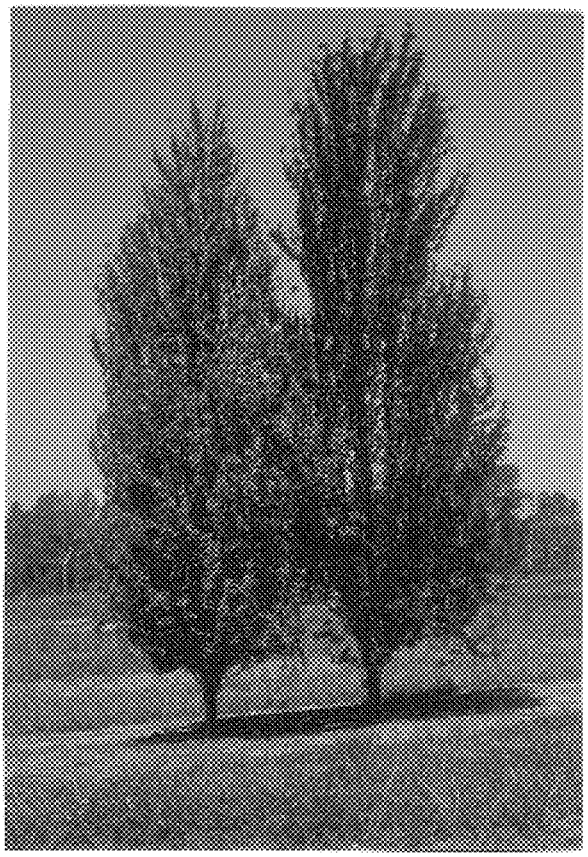
FIG. 2 shows a four-year-old tree of 'Corinthian Mauve' (left-hand-side) in comparison to 'Corinthian Rose' (right-hand-side) taken after flowering, showing the narrowly columnar tree architecture and the overall foliage color.
Figure 3:
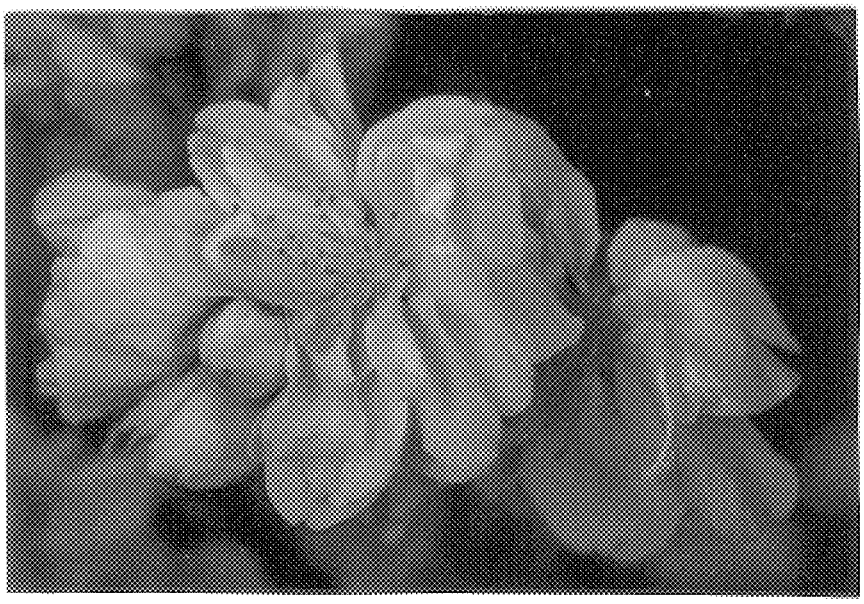
FIG. 3 shows a close-up photograph of the flower of 'Corinthian Mauve', showing the double flower structure and the representative pigmentation of a nearly mature flower.
Figure 4:
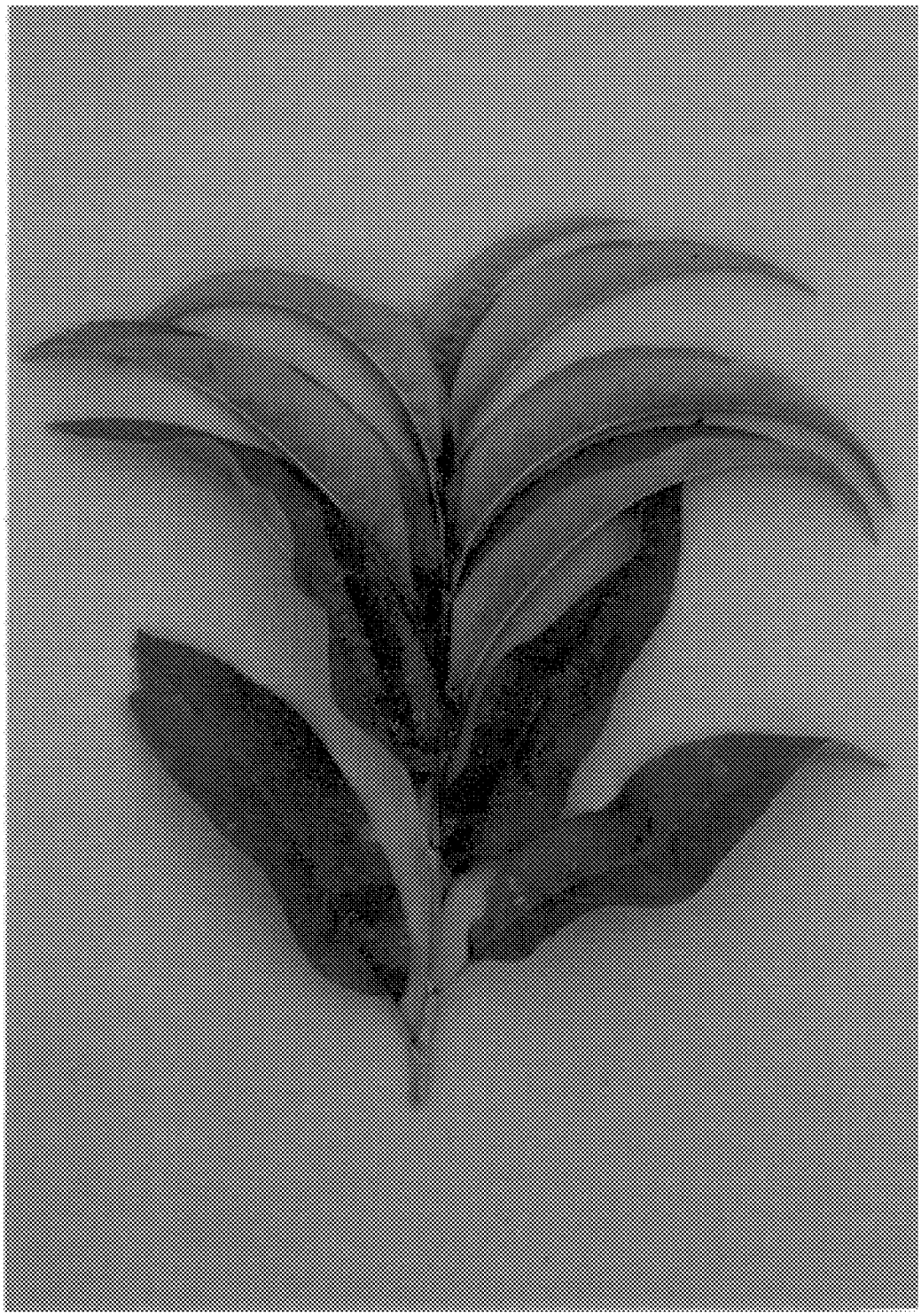
FIG. 4 is a close-up picture, taken May 18, 2000, showing the upper and lower surfaces of the leaves of 'Corinthian Mauve' attached to a rapidly growing shoot.

The following is a detailed description of the botanical and pomological characteristics of the subject peach. Color data are presented in Royal Horticultural Society Colour chart designations. Where dimensions, sizes, colors and other characteristics are given, it is to be understood that such characteristics are approximations of averages set forth as accurately as practicable.

The descriptions reported herein are from specimens grown at Raleigh, N.C. unless otherwise noted.

Tree:
- *Size.*—Large. 14–26 ft. height after 4 years of growth.
- *Vigor.*—Very vigorous.
- *Growth.*—Narrowly columnar.
- *Fruit production.*—Low.
- *Pest resistance.*—Susceptible to peach tree borer. Moderately resistant to bacteria leaf spot (Sandhills Research Station observations).

Trunk:
- *Size.*—Medium.
- *Texture.*—Medium to rough.
- *Color.*—Gray-green (197A).

Branches:
- *Size.*—Medium.
- *Surface.*—Smooth (new) to medium rough (old).
- *Lenticels.*—Medium size. Medium number.
- *Color.*—Bright green with slight red blush (actively growing new growth). Dormant one-year-old shoots gray-red (178-B). Dormant two-year-old shoots gray-brown (199-A).

Foliage:
- *Leaves.*—Large. Mature leaf length 12.6 cm; width 3.7 cm.
- *Form.*—Lanceolate. Acutely pointed. Leaf base medium pointed, cuneate.
- *Thickness.*—Medium.
- *Texture.*—Smooth to slightly rugose.
- *Margin.*—Crenate.
- *Petiole.*—Medium length.
- *Stipules.*—Present. Small.
- *Pubescence.*—Absent on both lower and upper surface.
- *Venation.*—Pinnate.
- *Glands.*—Average number 3. Varies from 2 to 5. Located on base of leaf and upper portion of petiole. Reniform.
- *Color.*—Upper surface—green to deep green (137A). Lower surface—dull green (137C).
- *Density.*—Dense.

Flower buds:
- *Size.*—Large.
- *Length.*—Medium.
- *Shape.*—Plump, slightly tapered at apex.
- *Color.*—Light brown.

Flowers:
- *Date of first bloom.*—March 15 to March 30. Varies yearly due to weather conditions.
- *Date of full bloom.*—March 25 to April 10. Varies yearly due to weather conditions.
- *Size.*—Large, showy. Diameter 2.0–2.5 cm.
- *Color.*—Dark pink to mauve (red 55D, newly emerged flowers, red purple 68A, mature flowers).
- *Reproductive organs.*—Stamens—erect, numerous. Pistils,—Usually one. Pollen—Normal and abundant Bright yellow.
- *Number of flowers per bud.*—One.
- *Number of petals per flower.*—Average 25.8.
- *Fertility.*—Self-fertile.

Fruit:
- *Maturity.*—Mid to late August.
- *Size.*—Very small. Less than 3.0 cm diameter.
- *Form.*—Slightly oblong.
- *Suture.*—Shallow.
- *Pubescence.*—Heavy.
- *Skin color.*—Yellowish-green with a trace (less than 10%) of red blush.
- *Flesh color.*—White.
- *Stone.*—Small, freestone.
- *Eating quality.*—Very poor.
- *Uses.*—None.

The Variety:

The most distinctive features of the variety are its narrowly columnar growth habit, and its double (multiple petals) mauve-colored flowers.

We claim:

1. A new and distinct variety of ornamental peach tree, substantially as illustrated and described, characterized by its narrowly columnar growth habit and large double mauve-colored flowers.

* * * * *